United States Patent
Towler et al.

(10) Patent No.: US 8,193,111 B2
(45) Date of Patent: Jun. 5, 2012

(54) PROCESS OR SYSTEM FOR DESORBING AN ADSORBENT BED

(75) Inventors: Gavin P. Towler, Des Plaines, IL (US); Charles P. Luebke, Des Plaines, IL (US); David N. Myers, Des Plaines, IL (US); Steven L. Krupa, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 286 days.

(21) Appl. No.: 12/509,182

(22) Filed: Jul. 24, 2009

(65) Prior Publication Data

US 2011/0021851 A1 Jan. 27, 2011

(51) Int. Cl.
*B01J 38/56* (2006.01)
*B01J 38/04* (2006.01)
*B01J 38/42* (2006.01)
*C10M 175/00* (2006.01)
*C07C 5/05* (2006.01)

(52) U.S. Cl. .............. 502/34; 502/31; 502/35; 208/183; 585/271; 585/323

(58) Field of Classification Search ............... 208/183, 208/203, 223, 228, 229, 301, 305, 370; 502/31, 502/32, 35, 34, 355, 406, 407, 410, 411, 502/450, 467, 820; 585/271, 277, 323, 332, 585/467

See application file for complete search history.

(56) References Cited

U.S. PATENT DOCUMENTS

| | | | |
|---|---|---|---|
| 3,660,967 A | 5/1972 | Collins et al. |
| 3,723,560 A | 3/1973 | Gleim et al. |
| 3,816,975 A | 6/1974 | Collins |
| 3,931,352 A | 1/1976 | Mikulicz |
| 5,098,668 A | 3/1992 | Callen et al. |
| 5,271,835 A | 12/1993 | Gorawara et al. |
| 5,391,527 A | 2/1995 | Kojima et al. |
| 5,489,732 A | 2/1996 | Zhang et al. |
| 5,672,798 A | 9/1997 | Zhang et al. |
| 6,548,721 B1 | 4/2003 | McCulloch et al. |
| 7,102,044 B1 | 9/2006 | Kulprathipanja et al. |
| 7,381,309 B1 | 6/2008 | Laricchia et al. |
| 2008/0194902 A1 | 8/2008 | Tsybulevski et al. |

OTHER PUBLICATIONS

Roeseler, UOP Alkylene™ Process for Motor Fuel Alkylation, Handbook of Petroleum Refining Processes, 2004, vol. 3rd Ed., Publisher: McGraw-Hill, pp. 1.25-1.31.

*Primary Examiner* — Jerry Lorengo
*Assistant Examiner* — Jennifer Smith
(74) *Attorney, Agent, or Firm* — Maryann Maas

(57) ABSTRACT

One exemplary embodiment can be a process for desorbing an adsorbent bed. The process can include passing a desorbent stream through the adsorbent bed to remove at least one of a nitrile compound and an oxygenate compound. Generally, the desorbent stream after desorbing is combined with a feed stream for an alkylation zone after a selective hydrogenation zone.

18 Claims, 2 Drawing Sheets

PROCESS OR SYSTEM FOR DESORBING AN ADSORBENT BED

FIELD OF THE INVENTION

This invention generally relates to a process or a system for desorbing an adsorbent bed.

DESCRIPTION OF THE RELATED ART

Often, an alkylation process may require the pretreatment of one or more olefins, typically C3-C5 olefins, used in the alkylation process. Typically, apparatuses are utilized to remove sulfur, and one or more diolefins, nitriles, and oxygenates, using processes such as extraction, hydrogenation, and adsorption.

Usually, an adsorption process uses an adsorbent to remove one or more nitriles and oxygenates. After the one or more nitriles and oxygenates are removed from an olefin stream, the adsorbent may be regenerated. The regeneration stream exiting the adsorbent bed often contains the desorbed one or more nitriles and oxygenates, and as such, the stream is required to be exported from the alkylation process. This exportation can require increased capital and operating costs.

Often, normal butane from an upstream or a downstream process may be utilized as the regeneration fluid. If insufficient normal butane is present, however, downstream products often can be fractionated to provide the requisite material. However, this again can require additional capital and operating costs for providing sufficient regenerant for desorption. Thus, recycling a stream within the process would be desirable to minimize or eliminate these additional costs.

SUMMARY OF THE INVENTION

One exemplary embodiment can be a process for desorbing an adsorbent bed. The process can include passing a desorbent stream through the adsorbent bed to remove at least one of a nitrile and an oxygenate compound. Generally, the desorbent stream after desorbing is combined with a feed stream for an alkylation zone after a selective hydrogenation zone.

Another exemplary embodiment may be a system for utilizing a desorbent stream. The system can include an extraction zone, a selective hydrogenation zone, a removal zone, and an alkylation zone. Generally, the removal zone includes a first adsorbent bed and a second adsorbent bed. A desorbent stream exiting one of the beds can be provided downstream of the hydrogenation zone and upstream of the alkylation zone.

A further exemplary embodiment can be a process for desorbing an adsorbent bed. The process can include passing a stream comprising at least about 30%, by mole, of at least one olefin through an extraction zone, a selective hydrogenation zone, and a removal zone, and combining an effluent stream from an adsorbent vessel with a desorbent stream exiting another adsorbent vessel before passing the combination to the alkylation zone.

The embodiments disclosed herein can provide several advantages, including using an internal regenerant source. Thus, the exportation of a spent regenerant may be eliminated. Instead, the spent regenerant can be recycled within the unit as a feed to an alkylation zone by, in one preferred embodiment, washing the spent regenerant in the adsorption zone to remove one or more nitriles and oxygenates from the spent regenerant stream before recycling to the alkylation zone. Additionally, the embodiments disclosed herein can provide a manufacturer with an alternative low cost regeneration scheme versus fractionation of an alkylation product.

Particularly, using a regenerant for the adsorption zone of make-up isobutane and optionally a portion of a recycle isobutane, which is often in excess in an alkylation zone, can utilize a desorbent having sufficient availability without requiring a fractionated product.

DEFINITIONS

As used herein, the term "stream" can be include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules. Additionally, characterizing a stream as, e.g., a "feed stream" or a "desorbent stream" can mean a stream including or rich in, respectively, at least one feed or desorbent.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 30%, and preferably about 50%, by mole, of a compound or class of compounds in a stream.

As used herein, the term "adsorbent" includes an absorbent, and relates, but is not limited to, absorption and/or adsorption. Similarly, the term "absorbent" includes an adsorbent, and relates, but is not limited to, absorption and/or adsorption.

As used herein, the terms "regenerant" and "desorbent stream" may be used interchangeably.

As used herein, the term "vapor" can mean a gas or a dispersion that may include or consist of one or more hydrocarbons.

As depicted, process flow lines in the figures can be referred to as lines or streams. Particularly, a line can contain one or more streams, and one or more streams can be contained by a line.

DETAILED DESCRIPTION

Figure 1:
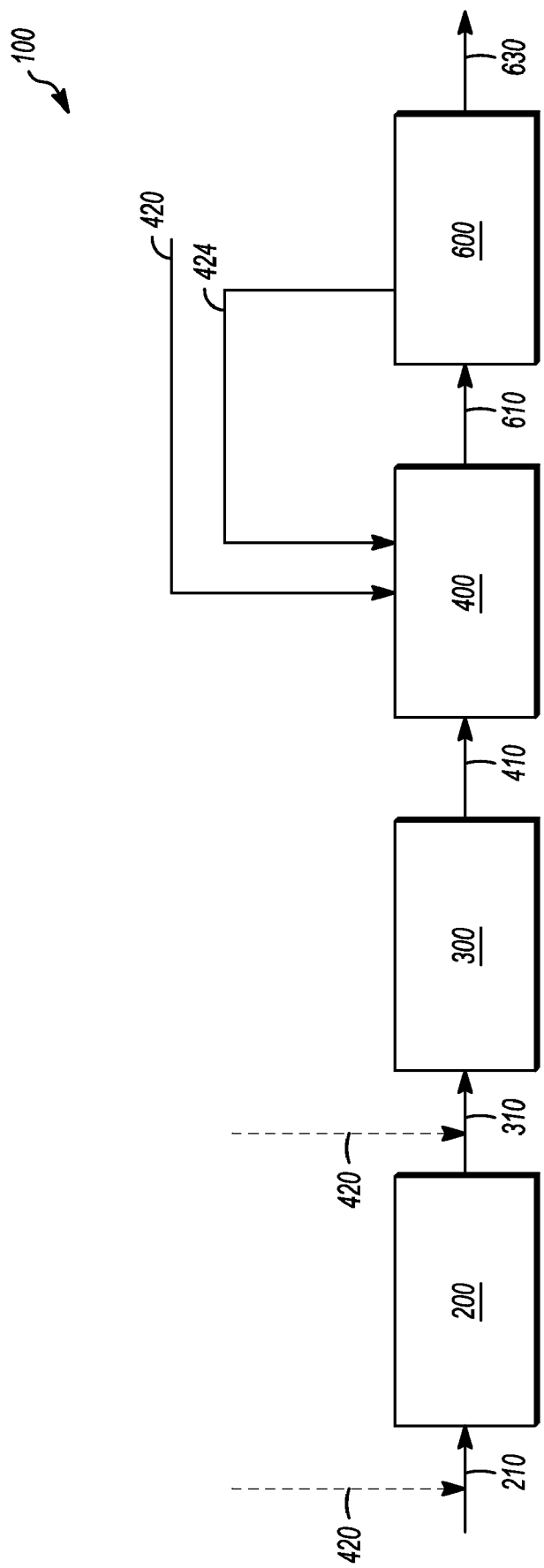
FIG. 1 is a schematic depiction of an exemplary chemical manufacturing unit or system.

Referring to FIG. 1, an exemplary chemical manufacturing unit or system 100 can include an extraction zone 200, a selective hydrogenation zone 300, a removal or an adsorption zone 400 (may hereinafter be simply referred to as "a removal zone 400"), and an alkylation zone 600. Typically, a feed stream 210 can be provided to the extraction zone 200. The extraction zone 200, in turn, provides a feed stream 310 to the selective hydrogenation zone 300. Afterwards, the selective hydrogenation zone 300 can provide a feed stream 410 to the removal or adsorption zone 400. A make-up isoparaffin stream 420 that can be utilized in the alkylation zone 600 may be provided directly to a dryer in the adsorption zone 400, as hereinafter described. The alternative locations for the make-up isoparaffin stream 420 as depicted by the dashed lines in FIG. 1 will be discussed hereinafter. Next, the removal or adsorption zone 400 can provide a hydrocarbon stream or a feed stream 610 to the alkylation zone 600. The alkylation zone 600, in turn, can provide an alkylation product stream 630 and a recycle isoparaffin stream 424 to the removal zone 400, as hereinafter described.

The extraction zone 200 can reduce the level of sulfur in the feed stream 210. Generally, the extraction zone 200 can include any suitable number of vessels, such as an amine absorber, an extraction vessel, an oxidation vessel, and a disulfide separator. Typically, the extraction zone 200 can remove hydrogen sulfide and carbonyl sulfide, and convert other sulfur compounds into, e.g., disulfide sulfur. Before the hydrocarbon effluent exits the extraction zone 200, the mercaptans and mercaptides can be removed to lower the sulfur concentration. Usually, the extraction zone 200 can utilize an aqueous alkaline solution, such as a caustic with a concentration of about 2-about 12%, by weight, to extract one or more sulfur compounds. The hydrocarbon streams in the extraction zone 200 are typically in a liquefied state and can be at a pressure of about 500-about 3,000 kPa and a temperature of about 20-about 50° C. Also, the aqueous alkaline solution can be maintained at a temperature of about 20-about 50° C. and a pressure of about 300-about 3,000 kPa. Typically, the feed stream 210 can have a sulfur concentration of about 1,000-about 2,000 ppm, by weight. Usually, the hydrogen sulfide can be reduced down to less than about 1 ppm, by weight, and other sulfur compounds, such as one or more mercaptans and/or disulfide sulfur, may be reduced to less than about 20 ppm, or even less than about 10 ppm, by weight, in the feed stream 310 provided to the selective hydrogenation zone 300. Suitable extraction zones are disclosed in, e.g., U.S. Pat. No. 7,381,309 B1.

The selective hydrogenation zone 300 can be any suitable hydrogenation zone using a catalyst that can reduce the amount of one or more dienes by conversion to one or more olefins. Suitable catalysts can include a group V-B metal, such as vanadium, niobium and/or tantalum, hydride. The metal hydride may exist in granular or powdered form and can be combined with a suitable porous refractory inorganic oxide carrier material, such as an alumina, a silica, a zirconia, a hafnia, a boria, or a mixture thereof The selective hydrogenation reaction can be undertaken at a pressure of about 10-about 4,500 kPa, a liquid hourly space velocity of about 0.2-about 5.0 $hr^{-1}$, a hydrogen concentration of about 300-about 3,500 normalized meter-cubed/meter-cubed, and a temperature of about 0-about 210° C. The selective hydrogenation reaction can have a conversion of one or more dienes, such as butadiene, of about 40%, by weight, which can be separated from the other hydrocarbon products and recycled back to the selective hydrogenation reactor, and a selectivity of conversion of olefin, e.g., butene, of about 90%, by weight. As a consequence, the hydrocarbon product exiting the selective hydrogenation zone 300 as the feed stream 410 can have a diene content of less than about 100 ppm, by weight. Suitable selective hydrogenation zones are disclosed in, e.g., U.S. Pat. No. 3,723,560.

The alkylation zone 600 can include any suitable catalyst for alkylating a feed. Generally, the feed stream 610 can include a one or more C3-C5 hydrocarbons, such as one or more C4 olefins and one or more C3-C5 paraffins, such as isobutane, to produce a C8 alkylate. Typically, the feed stream 610 can include about 30%, by mole, of at least one olefin. The paraffins can at least partially be provided by the streams 420 and 424 received by the upstream adsorption zone 400. In the adsorption zone 400, the streams 420 and/or 424 can be combined with the feed stream 410 to form the feed stream 610 provided to the alkylation zone 600. In one exemplary embodiment, the alkylation catalyst can include a refractory inorganic oxide impregnated with a monovalent cation such as an alkaline metal cation or an alkaline earth metal cation whose surface may be bound with hydroxyl groups. Optionally, the catalyst can also include a metal component such as nickel, platinum, palladium, and/or ruthenium. The catalyst may also contain one or more monovalent metals or alkaline earth metals, such as lithium, sodium, potassium, cesium, silver, copper, beryllium, magnesium, calcium, or barium, or a mixture thereof. Typically, after deposition of these metals and controlled calcination, the composite may be reacted with a metal halide, such as a halide of aluminum, zirconium, tin, tantalum, gallium, antimony, boron, or a mixture thereof. Suitable halides can include a fluoride, a chloride, a bromide, or a mixture thereof. The operating temperature as measured from the outlet of the reaction zone can be about −20-about 80° C. and a pressure of about 120-about 3,500 kPa. The catalyst to olefin weight ratio in the reaction zone can be about 1:1-about 1:25.Typically, it is preferred that the ratio of the isobutane to olefin is greater than about 1:1, and preferably about 2:1-about 5:1, or higher. Optionally, the products produced by the reaction can be separated by downstream fractionation into separate grades. Particularly, isobutane can be separated from the alkylate product. Exemplary alkylation zones are disclosed in, e.g., U.S. Pat. No. 5,489,732 and U.S. Pat. No. 5,672,798.Other exemplary alkylation catalysts can also be used, such as a solid phosphoric acid catalyst, as disclosed in, e.g., U.S. Pat. No. 6,548,721 B1.Optionally, the solid phosphoric acid catalyst can contain indium. The embodiments disclosed herein are particularly suited to a solid alkylation catalyst system.

The adsorption zone 400 can use any suitable adsorbent for removing one or more nitriles and oxygenates from the feed stream 410. Generally, such adsorption zones 400 can include one or more, preferably two or more, adsorbent beds. Any suitable molecular sieve can be utilized as the adsorbent, which can be a zeolitic molecular sieve. Generally, the molecular sieve can include a zeolite X, Y, L, or a combination thereof In addition, the adsorption conditions can be about 20-about 80° C. and a pressure of about 100-about 3,500 kPa. Generally, after adsorption, the adsorbent bed is desorbed. The regeneration conditions can include a temperature of about 200-about 320° C. and a pressure of about 100-about 3,500 kPa. Generally, the regenerant or desorbent stream is in a vapor phase. Typically, the desorbent stream can include a C3-C6 hydrocarbon stream. Preferably, the desorbent stream can include a C4 paraffinic stream typically containing a minimum of about 80%, by weight, C4 paraffins. In the instance that the alkylation zone 600 utilizes a solid phosphoric acid catalyst, the adsorbent stream can be a saturated paraffinic stream produced from the alkylation zone 600. Exemplary adsorbent beds and conditions are disclosed in, e.g., U.S. Pat. No. 5,271,835.

Figure 2:
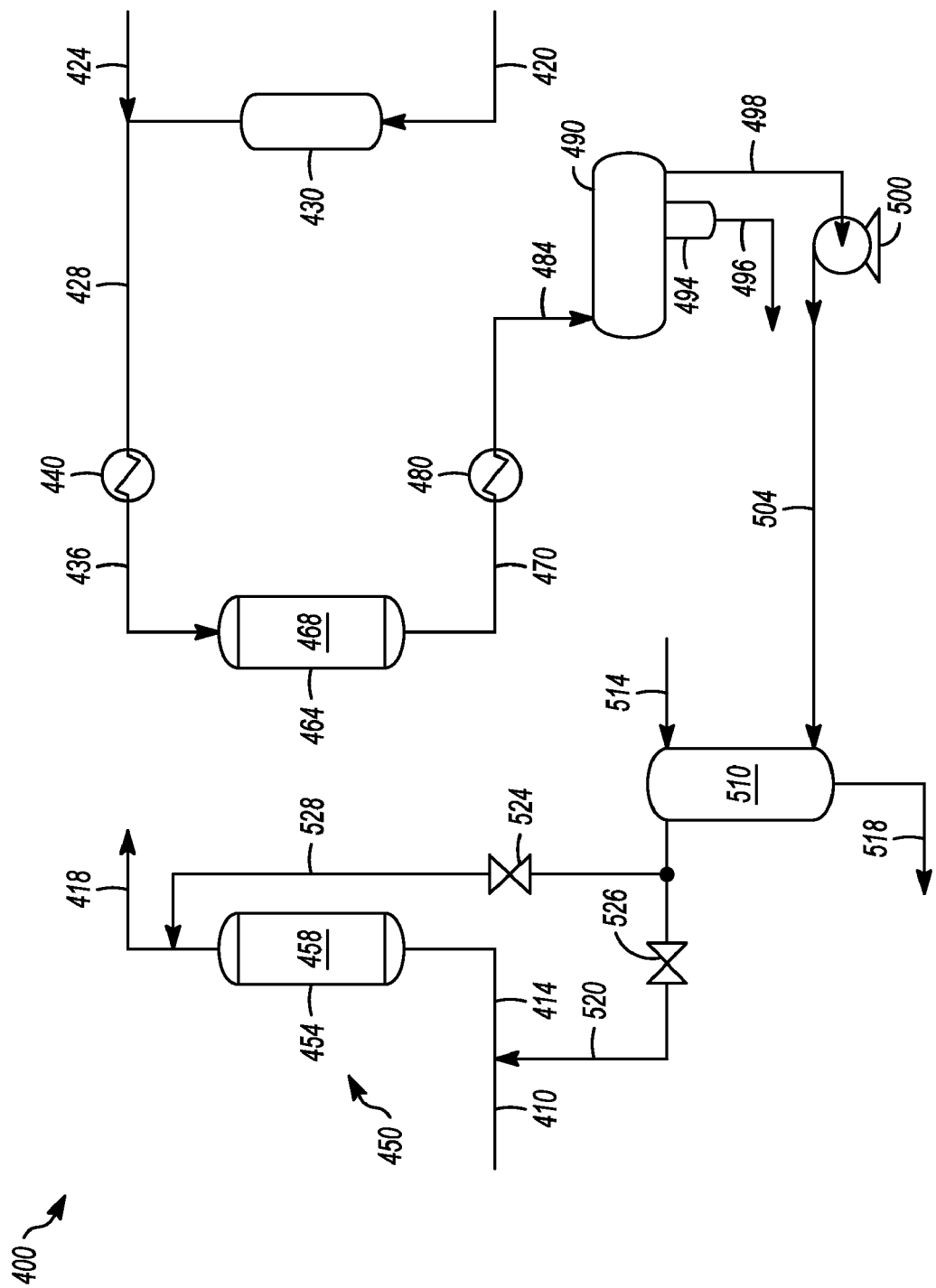
FIG. 2 is a schematic depiction of an exemplary removal or adsorption zone.

Referring to FIG. 2, one exemplary removal zone 400 can include a dryer 430, an exchanger 440, a plurality of adsorbent vessels 450, an exchanger 480, a receiver 490, a fluid transfer device 500, and a water wash vessel 510. Typically, the plurality of adsorbent vessels 450 can include a first vessel 454 and a second vessel 464. Typically, one vessel 454 can be adsorbing while the other vessel 464 is being regenerated.

During adsorbing, typically, the feed stream 410 is at a temperature of about 20-about 80° C., preferably about 40° C., and can be combined with a desorbent in a line 520, as hereinafter described. The combined stream 414 may be at a temperature of about 20-about 80° C., preferably about 40° C., and can be provided to the first vessel 454. Generally, the adsorbent bed or first adsorbent bed 458 can adsorb at a temperature of about 20-about 80° C., preferably about 40° C., and a pressure of about 850-about 950 kPa. Usually, the adsorption bed 458 can remove about 50-about 99.9%, typically about 90%, by weight, of the one or more nitriles and about 25-about 75%, typically about 50%, by weight, of the one or more oxygenates, based on the weight of the feed stream 410. Subsequently, a purified product or an adsorber effluent stream 418 having reduced levels of one or more nitriles and oxygenates can exit the first vessel 454. Typically, each of the vessels 454 and 464 has, respectively, an adsorbent bed or first adsorbent bed 458 and another or a second adsorbent bed 468.

During desorption, a make-up isoparaffin, typically isobutane, stream 420 and optionally a recycle isoparaffin, typically isobutane, stream 424 can be provided at a temperature of about 20-about 80° C., preferably about 40° C., as depicted in FIG. 1. The make-up isoparaffin stream 420 can be passed through the dryer vessel 430. Typically, the make-up isobutane dryer vessel 430 does not require a dedicated regeneration system. In one preferred embodiment, the make-up isobutane dryer vessel 430 can be regenerated by the vaporized make-up isobutane utilized for the regeneration of the adsorbent bed 468 during the cool down step of the adsorbent bed regeneration procedure.

After passing through the dryer vessel 430 for water removal, the make-up isoparaffin stream 420 can optionally be combined with a recycle isoparaffin stream 424 if the make-up isoparaffin stream 420 may be insufficient to meet the required regeneration conditions. Afterwards, the combined isoparaffin stream 428, typically at least about 80%, by mole, of one or more C4 paraffins and initially at a temperature of about 20-about 80° C., preferably about 40° C., can be heated with the exchanger 440 to about 200-about 320° C., preferably about 290° C., as a regenerant stream 436 for desorbing the second vessel 468. Moreover, the exchanger 440 can include a steam heater vaporizer followed by an electrical super-heater. Generally, the flow rate of the desorbent stream 436 can be set at about 5-about 50%, typically about 10%, by volume, of the combined stream 414 provided to the first vessel 454. The vaporized desorbent or regenerant stream 436 can exit the exchanger 440 and enter the second vessel 464 to remove one or more nitriles and oxygenates, and water from the adsorbent bed 468. The spent vapor phase regenerate stream 470, containing one or more nitriles and oxygenates, and/or water, can be condensed with water or air in the exchanger or cooler 480 to about 30-about 60° C., preferably about 40° C., before being routed to the receiver 490.

Typically, the receiver 490 forms a boot 494 for collecting water, which can exit as a water stream 496. In the water wash vessel 510, water can be contacted counter-currently against the spent regenerant containing one or more nitriles and oxygenates. A hydrocarbon stream 498 may also exit the receiver 490 and be provided to the fluid transfer device 500, which is typically a pump 500. A discharge stream 504 from the pump 500 can be provided to a water wash vessel 510. In some exemplary embodiments, the receiver 490 and fluid transfer device 500 can be optional. The water wash vessel 510 can remove one or more nitriles and oxygenates from the stream 504. Typically, a stream 514 including water can be provided to the water wash vessel 510 near the top while the discharge stream 504 can be provided near the bottom. The set point of the amount of the one or more nitriles in the stream 520 can control the rate of the water stream 514.

Typically, the stream 514 can be about 5% about 100%, typically about 30%, by volume of the flow of the stream 504.

The counter-current action of these two streams can result in a spent water stream 518, which may contain one or more nitriles and oxygenates, exiting the bottom of the water wash vessel 510. The hydrocarbon stream 520 can exit the water wash vessel 510, passing a valve 526 with a valve 524 closed, and be combined with the feed stream 410. Hence, the desorbent stream after being cleaned in the water wash vessel 510 can be combined with the feed stream 410 before passing through the first vessel 454 and entering the alkylation zone 600, as depicted in FIG. 1. Generally, all the streams in the adsorption zone 400 can be in a liquid phase except for the desorbent streams 436 and 470, which can be in a vapor phase.

In another exemplary embodiment, the washed desorbent stream 520 can be bypassed around the first adsorbent vessel 454. Particularly, a valve 524 can be opened and a valve 526 can be closed for allowing the washed desorbent stream 528 to be combined downstream of the first adsorbent vessel 454 with the adsorbent fluid stream 418. Typically, this bypassing can be done if another adsorbent vessel is downstream of the first adsorber vessel 454 so that the desorbent stream 528 can be passed through a subsequent adsorber before entering the alkylation zone 600. This bypassing is particularly suited in an adsorption zone 400 with at least three adsorption vessels.

What is more, alternate locations can receive the make-up isobutane instead, or in addition to, the adsorption zone 400 for providing at least a portion of the feed 610 to the alkylation zone 600. Referring to FIG. 1, the make-up isobutane stream 420 can be provided upstream of the extraction zone 200 and/or the hydrogenation zone 300, as depicted by the dashed lines. If all the isobutane can be provided upstream of the extraction zone 200 and/or the hydrogenation zone 300 instead of the adsorption zone 400, the required regenerate can be provided by the isobutane recycle stream 424. Usually, make-up isobutane stream can be provided by any suitable unit in a refinery or a chemical manufacturing plant.

The embodiments disclosed herein can provide an optimization between the water wash availability and utility costs versus the regenerant utility and adsorbent costs. For a site with minimum water availability, the design can utilize larger adsorber vessels and higher regenerant rates. For a site where water availability may not be an issue, the embodiments herein can have a minimum size of adsorbent vessels and regeneration rates. The optimization between wash water rate and regeneration system flow rate and adsorbent volume may be site specific. Moreover, the resultant nitrile and oxygenate removal level in the wash water stream can vary over a wider range, and particularly so for the oxygenate removal.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for desorbing an adsorbent bed, comprising:
   A) passing a desorbent stream through the adsorbent bed to remove at least one of a nitrile compound and an oxygenate compound wherein the desorbent stream after desorbing is combined with a feed stream for an alkylation zone after a selective hydrogenation zone, and
   B) water washing the desorbent stream after exiting the adsorbent bed and before entering the alkylation zone in a water wash vessel using a counter current action.

2. The process according to claim 1, wherein the desorbent stream comprises at least about 80%, by mole, one or more C4 paraffins.

3. The process according to claim 1, wherein the alkylation zone comprises a solid catalyst.

4. The process according to claim 1, wherein the adsorbent bed comprises a molecular sieve.

5. The process according to claim 4, wherein the molecular sieve comprises at least one of a zeolite X, Y, and L.

6. The process according to claim 1, wherein the step of water washing the desorbent stream further comprises:
   introducing a wash water stream to the water wash vessel at a first vessel location, introducing the desorbent stream to the water wash vessel at a second vessel location, and communicating the washed desorbent stream from the water wash vessel at a third vessel location, the first, second and third vessel locations selected to at least partially facilitate the counter current action; and,
   withdrawing a spent water stream containing one or more of nitriles and oxygenates from the water wash vessel.

7. The process according to claim 1, wherein the desorbent stream is combined with the feed stream before entering another adsorbent bed in a removal zone.

8. The process according to claim 1, wherein the desorbent stream is combined with an effluent from another adsorbent bed in a removal zone.

9. The process according to claim 8, wherein the removal zone comprises two or more adsorbent beds.

10. The process according to claim 1, further comprising condensing the desorbent stream after exiting the adsorbent bed.

11. The process according to claim 1, wherein the adsorbing bed operates at a temperature of about 20- about 80° C.

12. The process according to claim 1, wherein the desorbing is performed at a temperature of about 200- about 320° C.

13. The process according to claim 1, wherein the feed stream comprises at least about 30%, by mole, of at least one olefin.

14. The process according to claim 10, wherein the desorbent stream comprises at least about 80%, by mole, one or more C4 paraffins.

15. The process according to claim 1 wherein the step of washing the desorbent stream comprises using a water wash stream having a volume of between about 30% to 100% of the volume of the desorbent stream.

16. A process for desorbing an adsorbent bed, comprising:
   passing a stream comprising at least about 30%, by mole, of at least one olefin through an extraction zone, a selective hydrogenation zone, and a removal zone; and
   combining an effluent stream from an adsorbent vessel with a desorbent stream exiting another adsorbent vessel before passing the combination to an alkylation zone;
   washing the desorbent stream with water prior to combination with the effluent stream, the washing step comprising:
   introducing the desorbent stream into a water wash vessel at a first location;
   introducing the water wash stream into the water wash vessel at a second location that is distal from the first location and that causes the water wash stream and desorbent stream to engage in a countercurrent manner, the water wash stream removing one or more of nitriles and oxygenates from the desorbent stream;
   communicating a spent water wash stream containing one or more of nitriles and oxygenates from the water wash vessel; and,
   communicating the washed desorbent stream at a third location from the water wash vessel.

17. The process according to claim 1 wherein an adsorption zone includes a plurality of adsorption vessels, and wherein the step of combining the desorbent stream with a feed stream comprises opening a bypass valve to cause the washed desorbent stream to bypass a first of the plurality of adsorption vessels and to be combined with the feed stream downstream of the first adsorption vessel and upstream of a second adsorption vessel.

18. A process for desorbing an adsorbent bed, comprising:
   A) passing a desorbent stream through the adsorbent bed to remove at least one of a nitrile compound and an oxygenate compound;
   B) water washing the desorbent stream after exiting the adsorbent bed and before entering an alkylation zone in a water wash vessel using a counter current action;
   C) communicating a spent water stream from the water wash vessel, the spent water stream containing one or more of nitriles and oxygenates removed from the desorbent stream in the water wash vessel; and,
   D) selectively operating a bypass valve downstream of the water wash vessel to cause the washed desorbent stream exiting the water wash vessel to bypass a first adsorbent vessel and combine with a feed stream exiting the first adsorbent vessel before being introduced to a second adsorbent vessel, the first and second adsorbent vessels located upstream of the alkylation zone and downstream of a selective hydrogenation zone.

* * * * *